United States Patent
Koskan et al.

[11] Patent Number: 5,854,177
[45] Date of Patent: Dec. 29, 1998

[54] METHOD FOR ENHANCED HYDROPONIC PLANT PRODUCTIVITY WITH POLYMERIC ACIDS

[75] Inventors: Larry P. Koskan, Orland Park; Abdul Rehman Y. Meah, Justice; J. Larry Sanders, Lockport; Robert J. Ross, Elmhurst, all of Ill.

[73] Assignee: Donlar Corporation, Bedford Park, Ill.

[21] Appl. No.: 781,413

[22] Filed: Jan. 10, 1997

Related U.S. Application Data

[63] Continuation-in-part of Ser. No. 313,436, Sep. 27, 1994, Pat. No. 5,593,947, which is a continuation-in-part of Ser. No. 972,375, Nov. 5, 1992, Pat. No. 5,350,735.

[51] Int. Cl.$^6$ .................................................. A01N 37/06
[52] U.S. Cl. ............................................................ 504/320
[58] Field of Search ............................................. 504/320

[56] References Cited

U.S. PATENT DOCUMENTS

| | | | |
|---|---|---|---|
| 4,799,953 | 1/1989 | Danzig et al. | 71/98 |
| 4,813,997 | 3/1989 | Kinnersley et al. | 71/66 |
| 4,839,461 | 6/1989 | Boehmke | 528/363 |
| 4,863,506 | 9/1989 | Young | 71/113 |
| 4,863,898 | 9/1989 | Ashmead et al. | 514/6 |
| 4,923,500 | 5/1990 | Sylling et al. | 71/27 |
| 5,047,078 | 9/1991 | Gill | 71/11 |
| 5,209,768 | 5/1993 | Hughes | 504/313 |
| 5,350,735 | 9/1994 | Kinnersley et al. | 504/147 |

OTHER PUBLICATIONS

Kinnersley et al., Plant Growth Regulation 9:137–146 (1990).

Byrnes, Fertilizer Research 26:209–215 (1990).

*Primary Examiner*—S. Mark Clardy
*Attorney, Agent, or Firm*—Olson & Hierl, Ltd.

[57] ABSTRACT

Plant productivity in a hydroponic medium is enhanced by the addition of a water-soluble, non-biodegradable, non-peptidal polymeric acid having a molecular size larger than about 1,500 Daltons.

16 Claims, 3 Drawing Sheets

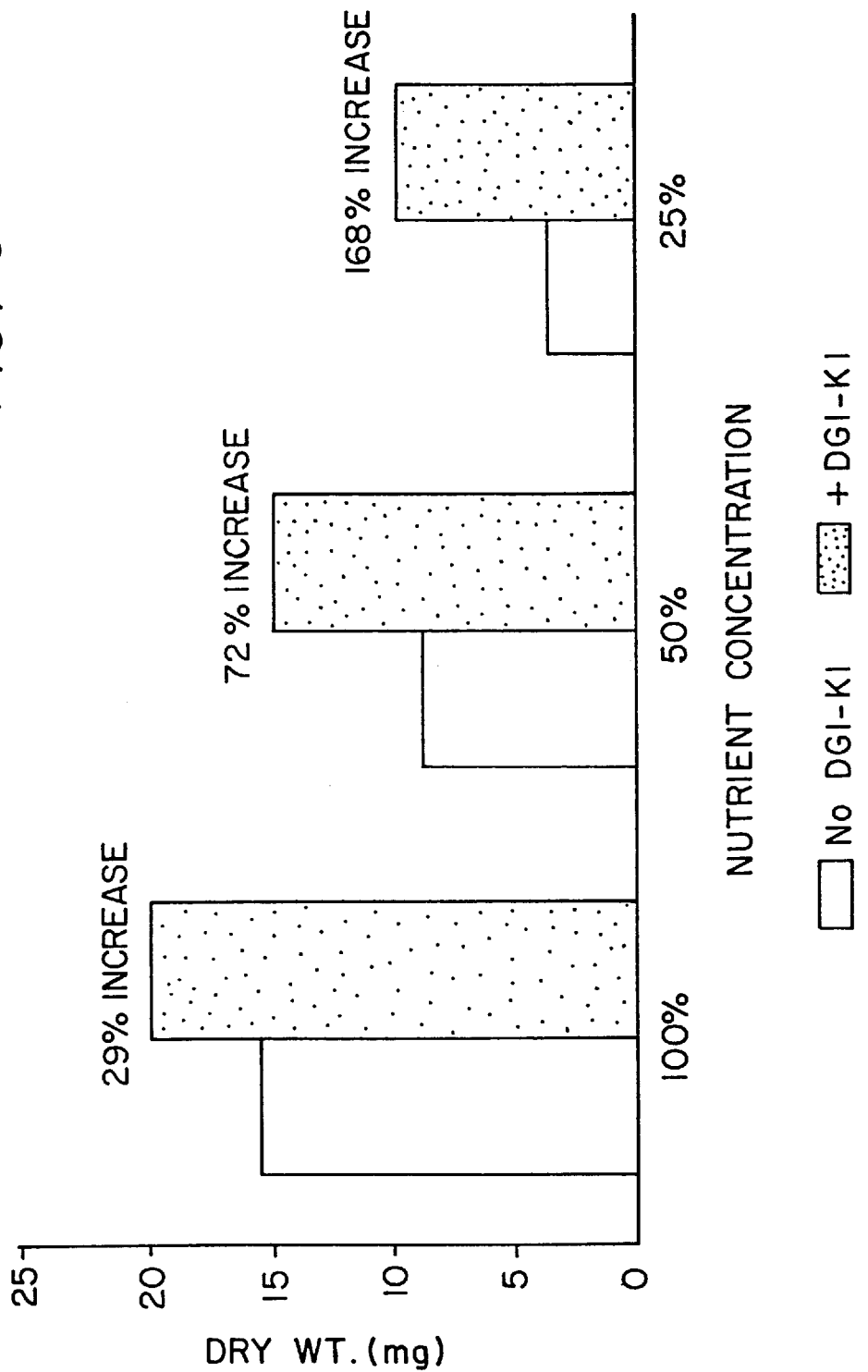

METHOD FOR ENHANCED HYDROPONIC PLANT PRODUCTIVITY WITH POLYMERIC ACIDS

CROSS-REFERENCE TO RELATED APPLICATION

This application is a continuation-in-part of U.S. Ser. No. 08/313,436, filed on Sep. 27, 1994, now U.S. Pat. No. 5,593,947, which is a continuation-in-part of U.S. Ser. No. 07/972,375, filed on Nov. 5, 1992, now U.S. Pat. No. 5,350,735.

TECHNICAL FIELD

This invention relates to a method for enhancing the productivity of plants in hydroponic growth medium. More particularly, this invention relates to absorption phenomena that facilitate the utilization of nutrients by plants through either seed, root or foliar pathways.

BACKGROUND OF THE INVENTION

Bio-degradable organic acids and oligomers thereof have been shown to promote plant growth. Typical promoters of plant growth are described by Kinnersley et al., *Plant Growth Regulation*, 9, pp. 137–146 (1990) (lactic acid and relatively low molecular weight oligomers of lactic acid); in U.S. Pat. No. 4,813,997 to Kinnersley et al. (oligomers of glycolic and/or L-lactic acid) and in U.S. Pat. No. 4,799,953 to Danzig et al. (oligomers of thiolactic and thioglycolic acids). The bio-degradable properties of long chain polymers of lactic acid are well-known in their historical use as internal sutures. All of the forgoing approaches to plant growth promotion appear to focus on coordination as a means for increasing plant uptake of compounds vital to the growth of the plant, e.g., micronutrients such as calcium, magnesium, sulfur, manganese, zinc, copper, iron, boron, and the like. The method of the present invention relies on non-biodegradable polymers which are too large to be absorbed by a plant, hence the mode of action probably is different than that described above.

A common approach to promoting plant growth has been, and continues to be, the use of nutrients (fertilizers), natural as well as synthetic. Synthetic nutrients usually provide nitrogen in a plant-usable form, such as urea for example, and/or inorganic nitrates, phosphates, or the like compounds. While such nutrients may be applied, more or less, at the convenience of the farmer, and may be applied as often as deemed desirable, the overuse of synthetic nutrients and the inefficient use of synthetic nutrients are major factors responsible for environmental problems such as eutrophication of groundwater, nitrate pollution, phosphate pollution, and the like. An overview of the undesirable effects of nitrogen fertilizer is presented by Byrnes, *Fertilizer Research*, 26, pp. 209–215 (1990).

To ameliorate the problems attendant to inefficient nutrient use and nutrient overuse, there is an ongoing desire and need for environmental and production reasons to increase fertilizer efficiency and to enhance plant productivity.

The present invention addresses and resolves these problems by methods which provide a more favorable environment for enhancing the utilization of nutrients by germinating or growing plants resulting in enhanced plant productivity in a hydroponic medium.

SUMMARY OF THE INVENTION

A method is provided for enhancing plant productivity in a hydroponic medium by achieving more efficient utilization of nutrients.

The present method comprises supplying to a plant in a hydroponic medium a productivity enhancing amount of a substantially water-soluble, non-biodegradable, non-peptidal polymeric acid having a molecular size larger than about 1,500 Daltons.

Particularly preferred for the present purposes are water-soluble, non-biodegradable polymers of acrylic acid with a molecular weight in the range of about 2,000 to about 15,000 Daltons.

This invention, when applied to plants in a hydroponic medium, beneficially provides stress protection and promotes nutrient uptake in environments containing salts present in concentrations that are normally toxic to plants. Further, a more favorable environment is provided to the plant which environment supplies the requisite nutrients at levels that are lower than usually are required with conventional fertilizers alone.

BRIEF DESCRIPTION OF THE DRAWINGS

In the drawings, there are shown photographic reproductions of corn plants treated in a particular manner alongside a control corn plant. In each case a yardstick (36 inches) is shown positioned between the photographed plants to indicate scale. In particular.

FIG. 5 is a graphical representation of growth enhancement with poly(aspartic acid) as reported in Example 15, below.

DETAILED DESCRIPTION OF PREFERRED EMBODIMENTS

Figure 1:
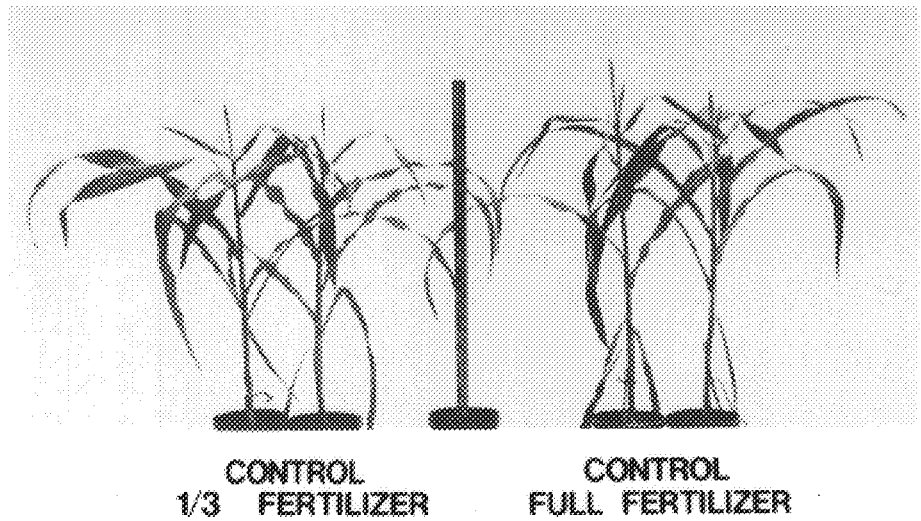
FIG. 1 shows corn plants 40 days after planting, and treated with one-third of the recommended fertilizer dosage alongside a corn plant treated with the recommended dosage for the same fertilizer.
Figure 2:
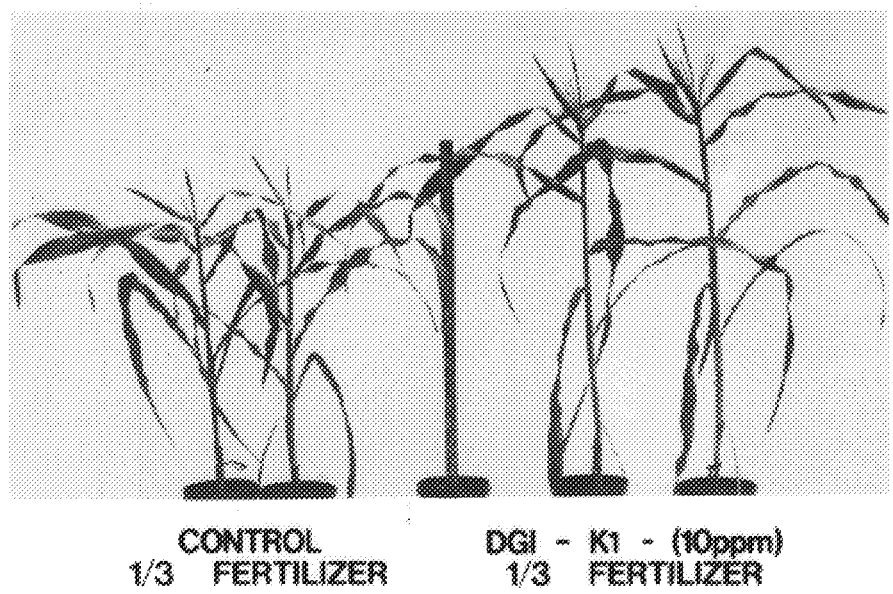
FIG. 2 shows a corn plant 40 days after planting, one treated with one third of the recommended fertilizer dosage alongside a corn plant similarly treated with the same fertilizer but also with 10 parts per million by weight of poly(aspartic acid)
Figure 3:
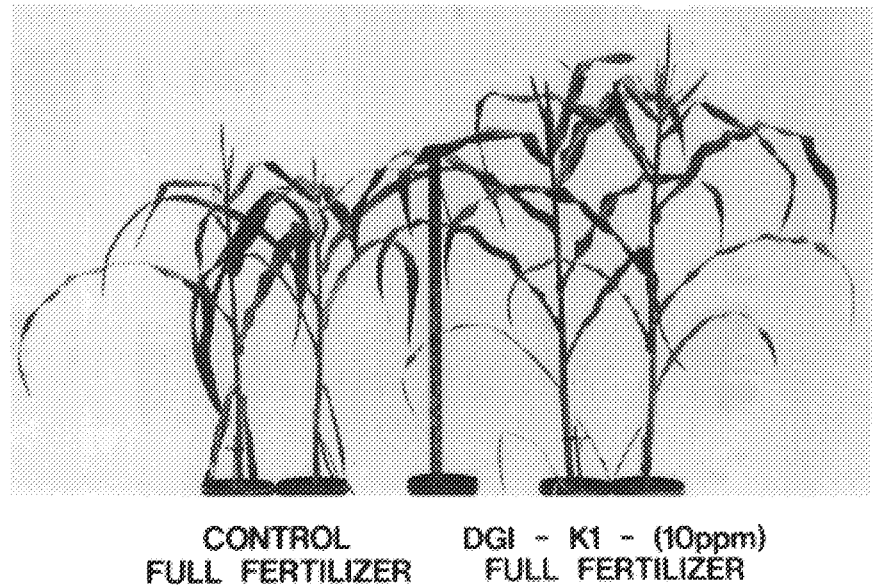
FIG. 3 shows corn plants 40 days after planting, both treated with the recommended fertilizer dosage and one plant also with 10 parts per million by weight of poly (aspartic acid)
Figure 4:
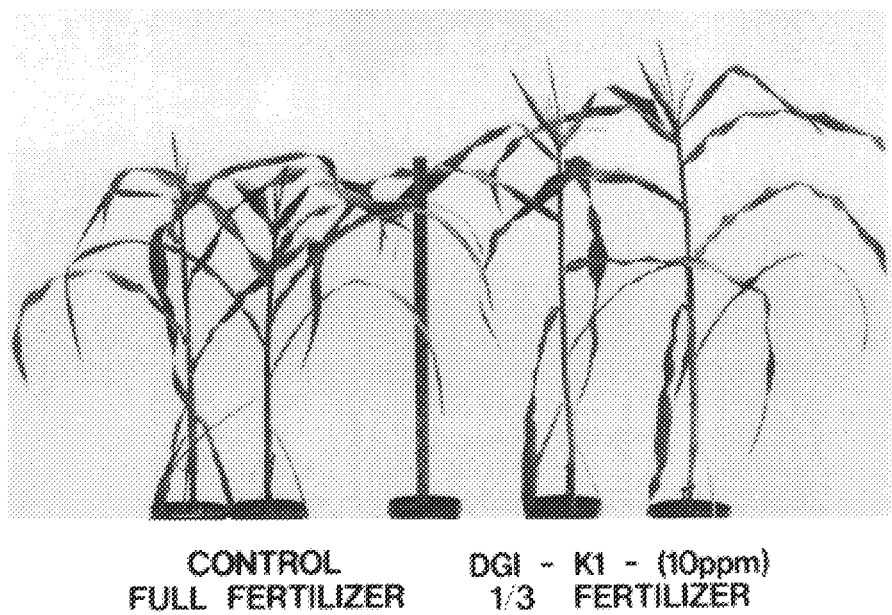
FIG. 4 shows corn plants 40 days after planting, one treated with the recommended fertilizer dosage and the other with one-third of the recommended fertilizer dosage but also with 10 parts per million by weight of poly(aspartic acid)

The present invention is predicated on the discovery that polymeric acids, and non-peptidal polymeric acids in particular, of a molecular size too large to enter a plant nevertheless provide a favorable environment for enhanced plant productivity. The more efficient utilization of nutrients can be realized in the presence of the polymeric acid inasmuch as relatively lower nutrient dosages can be relied upon to provide the requisite nutrients to the plant in a hydroponic medium.

The present invention is directed to a method for enhancing plant productivity in hydroponic medium. Enhanced plant productivity is achieved by making nutrients more readily available to the plant through its seed, root feeding zone, foliar absorption and translocation mechanisms, growth medium or combinations of the foregoing.

The term "enhanced plant productivity" as used herein means that one or more of the following factors is achieved:

increased growth rate, increased biomass, higher yields and quality (i.e., increased protein content), accelerated rate of root formation, increased tillering, increased chlorophyll concentration and the like indicia.

In general, the polymeric acids can be supplied to the plant in a hydroponic medium in the form of aqueous liquids or in water-soluble substantially solid form.

Preferably, aqueous nutrient solutions supplied to the plant contain at least about 10 parts per billion (ppb) by weight, preferably about 0.1 to about 1,000 parts per million (ppm) by weight, more preferably about 1 to about 500 ppm by weight of the polymeric acid. Such solutions can be introduced into hydroponic gardening or farming systems in an amount as is discussed in below.

Aqueous solutions containing the polymeric acid also enhance plant productivity under stressful growth limiting conditions, e.g., in growth medium that contains salts or metal ions in concentrations normally toxic to plants or in growth medium depleted in certain nutrients.

The polymeric acids can also be supplied to the hydroponic growth medium in substantially solid form, alone or in combination with nutrients. Dry granular or pelleted forms of the polymeric acids can be impregnated or pre-formed as carriers of nutrients and can then be supplied to plant in the hydroponic growth medium.

The non-biodegradable, non-peptidal polymeric acids, to be suitable for the practice of the present invention, must be substantially water-soluble, and have a molecular size sufficiently large to preclude absorption into the plant. To that end, the polymeric acids suitable for the present purposes, while hydrophilic, have a Mw larger than about 1,500 Daltons.

Polymeric acids having a molecular size in excess of about 100,000 Daltons usually do not exhibit adequate solubility in water for the present purposes. Thus a polymeric acid of a molecular size not larger than about 100,000 Daltons is presently preferred. A particularly suitable molecular size is in the range of about 2,000 to about 100,000 Daltons.

Illustrative are non-peptidal polymeric acids derived from a monomer which is a member of the group consisting of tartaric acid, acrylic acid, maleic acid, fumaric acid, 2-acrylamido-2-methylpropanesulfonic acid, itaconic acid, and methacrylic acid. In addition, polymeric acids useful for present purposes include derivatized version of the aforementioned polymers, e.g. polymers having a pendant group selected from the group consisting of a sulfonate, a sulfinate, a phosphonate, a phosphinate, a hydroxyl and an alkyl group containing up to about 20 carbon atoms. Inasmuch as the aforementioned alkyl group is hydrophobic, the amount of such groups in a given polymer is such as not to materially affect the solubility of the polymer.

Particularly preferred for the present purposes are polymers such as water-soluble polycarboxylates such as polyacrylic acid, polymaleic acid, polytartaric acid and their co-polymers. Random co-polymers as described above are within the purview of the present invention as are block co-polymers composed of several repetitive units.

Counterions for the polymeric acids include, but are not limited to, the alkali metal cations, preferably $Na^+$, $K^+$, and $Li^+$; alkali earth metal cations, preferably $Mg^{++}$, $Ca^{++}$ and $Ba^{++}$; transitional metal cations, preferably $Zn^{++}$, $Co^{++}$, $Fe^{++}$ and $Fe^{+++}$; and $NH_4^+$.

Particularly well-suited for the practice of the present invention are polymers of acrylic acid having a molecular size of about 2,000 to about 15,000 Daltons.

The aforesaid polymeric acids increase the efficiency of fertilizers and the utilization of nutrients, both natural and synthetic. The nutrients can be those found naturally in the hydroponic plant growth medium or can be those which are added to the medium or can be those that are residual nutrients from previous nutrient treatments. More efficient utilization by the growing plants of both macronutrients, such as but not limited to, nitrogen (N), phosphorus (P), potassium (K) and micronutrients, such as but not limited to, calcium (Ca), magnesium (Mg), sulfur (S), zinc (Zn), iron (Fe), manganese (Mn), boron (B), cobalt (Co), molybdenum (Mo), copper (Cu) and nickel (Ni) is accomplished by employing the polymeric acids of this invention.

There are many uses and applications for the present invention in its various aspects. Illustrative are uses in aquaculture, hydroponics, water reclamation (e.g. lakes with relatively high salt concentrations, etc.), and the like.

The polymeric acid can be made available to the plant in hydroponic medium as a separate treatment or supplied to the plant together with a plant nutrient or a combination of plant nutrients.

The present invention is further illustrated by the following examples which demonstrate more efficient utilization of plant growth nutrients in a hydroponic medium by employing non-peptidal polymeric acids.

EXAMPLE 1

Effect of Non-peptidal Polymeric Acids to Increase Efficiency of Limited Amounts of Plant Nutrients Duckweed (*Lemna minor L.*) was grown in an aqueous solution containing relatively low levels of nutrients as shown in the following Table I.

TABLE I

LOW NUTRIENT COMPOSITION

| Nutrient Element | Concentration (ppm as element) |
|---|---|
| Nitrogen (N) | 12.5 |
| Phosphorus (P) | 3 |
| Potassium (K) | 12 |
| Calcium (Ca) | 10 |
| Magnesium (Mg) | 4 |
| Sulfur (S) | 14 |
| Iron (Fe) | 1 |
| Water, q.s. | |

Tests were performed in which the plants were grown in separate flasks under controlled conditions employing the low nutrient solution which was enhanced by the addition of 50 ppm by weight of a selected polymeric acid, identified as Compound A or B in Table II, below.

TABLE II

POLYMERIC ACID

A. polyacrylic acid, sodium salt
   (Mw about 2,000 Daltons)
B. polyacrylic acid, sodium salt
   (Mw about 4,500 Daltons)

For evaluating stress protection, a similar series of tests were performed in which the plants were grown employing each of the foregoing compositions to which 3 ppm of $Cu^{++}$ ion was also added. For each test, the enhanced nutrient solution was adjusted to pH 6.7±0.1 and five replications were performed, both with and without the added copper.

A single duckweed plant at the three-frond stage was placed in each flask. Each flask was then incubated under continuous light in a greenhouse at a temperature of about 28°±2° C. for three days. The plants were then harvested, oven dried and weighed. The average dry weight of the plant is reported in Table III, below. All reported values represent an average of five replicates.

TABLE III

STRESS PROTECTION AND PLANT PRODUCTIVITY

| Compound | AVERAGE BIOMASS (mg) | |
|---|---|---|
| | no additional $Cu^{++}$ | 3 ppm $Cu^{++}$ |
| None (Control) | 9.648 | 3.338 |
| A | 14.534 | 6.204 |
| B | 13.894 | 6.932 |

The data show that the addition of each of the polymeric acids to each low level nutrient solution resulted in enhanced plant productivity based on an average biomass increase of more than 50% for compound A and 44% for Compound B. The data also show that the stressing effect of copper toxicity limited plant growth to 35% as compared to the plant growth at non-toxic copper levels. The presence of each polymeric acid afforded a degree of stress protection by enhancing plant productivity to 43% for Compound A and 50% for Compound C.

EXAMPLE 2

Effect of Non-peptidal Polymeric Acids to Increase Efficiency of Limited Amounts of Plant Nutrients Duckweed (*Lemna minor L.*) was grown in an aqueous solution containing relatively low levels of nutrients as shown in the following Table IV.

TABLE IV

NUTRIENT COMPOSITION

| Nutrient Element | Concentration (ppm as element) |
|---|---|
| Nitrogen (N) | 25 |
| Phosphorus (P) | 6 |
| Potassium (K) | 24 |
| Calcium (Ca) | 20 |
| Magnesium (Mg) | 8 |
| Sulfur (S) | 28 |
| Iron (Fe) | 2 |
| Water, q.s. | |

Tests were performed in which the plants were grown in separate flasks under controlled conditions employing the nutrient solution which was enhanced by the addition of 50 ppm by weight of a selected polymeric acid, identified as Compounds A and C through F in Table V, below.

TABLE V

POLYMERIC ACID

A. polyacrylic acid, sodium salt (Mw about 2,000 Daltons)
C. polyacrylic acid, sodium salt (Mw about 15,000 Daltons)
D. co-polymer of polyacrylic acid-maleic acid, sodium salt, sold under name Sokalan ® CP5, BASF (Mw about 70,000 Daltons)

TABLE V-continued

POLYMERIC ACID

E. co-polymer of carboxylate-sulfonate (non-ionic), sold under name Acumer ® 3100, Rohm and Haas (Mw about 4,500 Daltons)
F. polymer of phosphonocarboxylic acid, sold under name Belcene ® 494, FMC (Mw about 4,500 Daltons)

For evaluating stress protection, a similar series of tests were performed in which the plants were grown employing each of the foregoing compositions to which 4 ppm of $Cu^{++}$ ion was also added. For each test, the enhanced nutrient solution was adjusted to pH 6.7±0.1 and five replications were performed, both with and without the added copper.

A single duckweed plant at the three-frond stage was placed in each flask. Each flask was then incubated under continuous light in a greenhouse at a temperature of about 28°±2° C. for three days. The plants were then harvested, oven dried and weighed. The average dry weight of the plant is reported in Table VI, below. All reported values represent an average of two experiments with four replicates. In addition, a second set of controls (without polymer added) were run in a nutrient solution containing five times the nutrient concentration of the other experiments.

TABLE VI

STRESS PROTECTION AND PLANT PRODUCTIVITY

| Compound | AVERAGE BIOMASS (mg) | |
|---|---|---|
| | no additional $Cu^{++}$ | 4 ppm $Cu^{++}$ |
| None (Control) | 8.0 | 5.1 |
| A | 10.2 | 8.4 |
| C | 10.8 | 9.0 |
| D | 11.4 | 8.7 |
| E | 10.1 | 8.0 |
| F | 10.8 | 7.6 |
| None, with 5X nutrients (Control) | 11.5 | 7.9 |

The data in Table VI show that the addition of each of the polymeric acids to each nutrient solution resulted in enhanced plant productivity based on an average biomass increase of more than 25% for all compounds tested. The data also show that the stressing effect of copper toxicity limited plant growth to 64% as compared to the plant growth at non-toxic copper levels. The presence of each polymeric acid afforded a degree of stress protection by enhancing plant productivity to 830% for Compounds A and C.

EXAMPLE 3

Effect of Non-peptidal Polymeric Acids to Increase Efficiency of Limited Amounts of Nutrients in Tomato Plants A set of three tomato plants were grown hydroponically, in 7 liter aerated pots in the low nutrient solution utilized in Example 2. A second set of three tomato plants were grown in a 5X nutrient solution, known as normal nutrient solution. In addition, two sets of three tomato plants were grown in low and normal nutrient solutions with the additional polymeric acid, Compound B (Table II above), at a level of 50 ppm.

The plants were all grown in a greenhouse at 28° C., with supplemental halide lighting (500 lux) for 15 days without replacement of the nutrient solution or polymeric acid. At the end of the 15 days, the solutions were replaced with fresh solutions of the same initial composition every three days, and for an additional 15 days. The solutions were maintained daily at a pH in the range of about 5.5 to about 6.0 by titration.

The plants were harvested after a total of 30 days then dried and weighed. For each set of three plants, the results were averaged and reported in Table VII below.

TABLE VII

PLANT PRODUCTIVITY FOR TOMATO PLANTS

| | AVERAGE BIOMASS (mg) | |
|---|---|---|
| Compound | low nutrients | normal nutrients |
| None (Control) | 100 | 650 |
| B | 630 | 1000 |

The results on Table VII demonstrate that the polymeric acid, Compound B, enhanced the productivity of tomato plants grown with limiting amounts of nutrients to a level about the same as that of plants grown in normal nutrient level solutions. Thus the plants grew to the same size using 80% less fertilizer (nutrients). In addition, the polyacrylic acid also enhanced the productivity of tomato plants by about 65% when added to media containing normal nutrient levels.

The foregoing specification and the Examples are intended to illustrate the present invention, but are not to be taken as limiting.

We claim:

1. A method for enhancing plant productivity which comprises supplying to a plant in a hydroponic medium a productivity enhancing amount of a substantially water-soluble, non-biodegradable non-peptidal polymeric acid, the polymeric acid having a molecular size larger than about 1,500 Daltons.

2. The method of claim 1 wherein the polymeric acid is polyacrylic acid.

3. The method of claim 2 wherein the polyacrylic acid has a molecular size in the range of about 2,000 to about 15,000 Daltons.

4. The method of claim 1 wherein the molecular size of the polymeric acid is about 2,000 to about 100,000 Daltons.

5. The method of claim 1 wherein plant nutrients are supplied to the plant together with the polymeric acid.

6. The method of claim 1 wherein the productivity enhancing amount of the polymeric acid is supplied to the plant as an aqueous solution containing at least about 10 parts per billion of the polymeric acid.

7. The method of claim 1 wherein the productivity enhancing amount of the polymeric acid is supplied to the plant as an aqueous solution containing about 0.1 to about 1,000 parts per million of the polymeric acid.

8. The method of claim 1 wherein the polymeric acid is polyacrylic acid having a molecular size of about 2,000 Daltons.

9. The method of claim 1 wherein the polymeric acid is polyacrylic acid having a molecular size of about 4,500 Daltons.

10. The method of claim 1 wherein the polymeric acid is polyacrylic acid having a molecular size of about 15,000 Daltons.

11. The method of claim 1 wherein the polymeric acid is in the form of a salt having a substantially non-toxic counterion selected from the group consisting of an alkali metal, an alkali earth metal, a transition metal, and ammonium.

12. The method of claim 1 wherein the polymeric acid is derived from a monomer selected from the group consisting of tartaric acid, acrylic acid, maleic acid, fumaric acid, 2-acrylamido-2-methylpropanesulfonic acid, itaconic acid, and methacrylic acid.

13. The method of claim 12 wherein the polymeric acid includes a polymer derivative having a pendant group selected from the group consisting of a sulfonate, a sulfinate, a phosphonate, a phosphinate, a hydroxyl and an alkyl group containing up to about 20 carbon atoms.

14. The method of claim 1 wherein the polymeric acid is a water-soluble polycarboxylate selected from the group consisting of polyacrylic acid, polymaleic acid, polytartaric acid and a co-polymer thereof.

15. The method of claim 14 wherein the co-polymer is a random co-polymer.

16. The method of claim 14 wherein the co-polymer is a block co-polymer.

* * * * *